United States Patent
Jacobs et al.

[19]

[11] Patent Number: 5,994,139
[45] Date of Patent: Nov. 30, 1999

[54] STABLE HEMATOLOGY CONTROL COMPOSITION AND METHOD OF USE

[75] Inventors: Dana B. Jacobs, Cooper City; Ted Gerula, Ft. Lauderdale; Wayne M. Goldson, Pembroke Pines; Michael N. Elliott, Cooper City, all of Fla.

[73] Assignee: Coulter International Corp., Miami, Fla.

[21] Appl. No.: 09/056,265

[22] Filed: Apr. 7, 1998

[51] Int. Cl.[6] ................................................. G01N 33/48
[52] U.S. Cl. ...................... 436/10; 436/8; 436/18; 436/63; 436/66; 436/176; 436/179; 252/408.1
[58] Field of Search .................... 436/8, 10, 16, 436/18, 63, 66, 174, 176, 179; 435/2, 4, 29; 252/408.1

[56] References Cited

U.S. PATENT DOCUMENTS

| | | | |
|---|---|---|---|
| 2,656,508 | 10/1953 | Coulter | 324/71.1 |
| 3,502,974 | 3/1970 | Coulter et al. | 324/71.1 |
| 3,574,137 | 4/1971 | Decasperis | 436/10 |
| 3,640,896 | 2/1972 | De Casperis | 436/10 |
| 3,873,467 | 3/1975 | Hunt | 436/10 |
| 4,199,471 | 4/1980 | Louderback et al. | 436/11 |
| 4,219,440 | 8/1980 | Runck et al. | 436/10 |
| 4,324,686 | 4/1982 | Mundschenk | 436/10 |
| 4,358,394 | 11/1982 | Crews et al. | 436/10 |
| 4,390,632 | 6/1983 | Carter, II | 436/10 |
| 4,436,821 | 3/1984 | Ryan | 436/10 |
| 4,579,824 | 4/1986 | Louderback et al. | 436/10 |
| 4,698,312 | 10/1987 | Wong et al. | 436/10 |
| 4,704,364 | 11/1987 | Carver et al. | 436/10 |
| 4,753,888 | 6/1988 | Chiang | 436/11 |
| 5,008,201 | 4/1991 | Ryan | 436/10 |
| 5,262,327 | 11/1993 | Ryan | 436/10 |
| 5,270,208 | 12/1993 | Ryan | 436/10 |
| 5,320,964 | 6/1994 | Young et al. | 436/10 |
| 5,380,664 | 1/1995 | Carver et al. | 436/10 |
| 5,512,485 | 4/1996 | Young et al. | 436/10 |
| 5,529,933 | 6/1996 | Young et al. | 436/10 |
| 5,935,857 | 8/1999 | Riesgo et al. | 436/18 |

*Primary Examiner*—Maureen M. Wallenhorst
*Attorney, Agent, or Firm*—Mitchell E. Alter

[57] ABSTRACT

The present invention relates to a hematology control product for automated hematology instruments containing an aqueous solution of at least one blood cell analog, an absorbance agent in an amount sufficient to simulate a hemoglobin concentration, and a stabilizing agent in an amount sufficient to stabilize the size of the blood cell analog when the control product is subjected to temperature ranging from −15° C. to 45° C. The control product does not require controlled temperature storage for product stability. In addition, a novel method of using a hematology control product is provided wherein the control product contains a single blood cell analog and is used to simulate both red blood cells and white blood cells on an automated hematology instrument.

14 Claims, 3 Drawing Sheets

STABLE HEMATOLOGY CONTROL COMPOSITION AND METHOD OF USE

BACKGROUND OF THE INVENTION

1. Technical Field of the Invention

The present invention relates to a hematology control product for use in automated hematology instruments using electronic, optical and absorption means. The hematology control product provides quality assurance of proper instrument operation.

2. Discussion of the Prior Art

Quality control is a necessary and routine procedure in clinical hematology. Hematology control products are widely used as a quality control material to monitor automated electronic instrument determinations of blood cell values in various established clinical hematology procedures. Specific blood cell measurements that are made by these procedures include white blood cell count (WBC), red blood cell count (RBC), hematocrit (HCT) hemoglobin content (Hgb), mean corpuscular volume (MCV), mean corpuscular hemoglobin concentration (MHC) and platelet parameters such as platelet count. The function of a hematology control product is to provide a means of ascertaining the accuracy and precision of the instrument used to make these specific blood cell measurements.

Hematology control products for the above clinical hematology procedures are known. In these prior art products, a blood cell analog having known attributes is prepared from human or animal cells, or synthetic particles, such as latex, and maintained in an aqueous suspension to simulate human blood. Typically, the control products are required to be stored at a temperature between about 2° C. and 8° C. If the control product exceeds this temperature range, the product will not be suitable as a hematology control product because of product deterioration. Usually, stabilized red blood cells re used to simulate red blood cells in whole blood and fixed white or red lood cells are used to simulate white blood cells in whole blood.

With the numerous types of automatic hematology instruments for particle counting now available, quality control using hematology control products is necessary since the possibility of malfunctioning of the instrument is ever present. Although this disclosure will be directed primarily to embodiments involving the use of automated hematology instruments of the Coulter type, as exemplified by U.S. Pat. Nos. 2,656,508 and 3,502,974. It should be understood that the hematology control product and the method of use described herein finds wide application with hematology instruments generally. Accordingly, the term "automated hematology instrument" as used herein, should be understood to include, in addition to Coulter type hematology instruments, any other type of automated hematology instrument which discriminates among particles by the use of measurements of direct current (DC) resistance, radio frequency (RF) resistance, absorbance, light scatter, fluorescence and combinations thereof.

Automated hematology instruments are now being widely used in developing countries. However, many of these countries lack adequate controlled temperature shipping and storage facilities. The lack of such facilities has presented special problems for hematology control products. Typically, the control products require controlled shipping temperatures to remain useful by the time when the customer receives it. More specifically, if the control product freezes and thaws during shipping or is subjected to temperatures greater than 10° C., the control product will deteriorate and will not work for quality control purposes. The freeze and thaw causes the red blood cells, white blood cells and platelets, or analogs thereof, to change in size or to lyse, so that the control product is no longer useful for quality control measurements. Similarly, the elevated temperature causes the red blood cells, white blood cells and platelets, or analogs thereof, to either be destroyed or to change in size so that he control product is no longer useful for quality control measurements. In addition, the control product needs to have open vial stability, without refrigeration, because the laboratory might not ave sufficient refrigerated storage for the control product. More specifically, he commercial control product will rapidly deteriorate when not maintained at roper storage conditions, 2° C. to 8° C., making it unsuitable for quality control measurements. Consequently, there exists a need for a new hematology control product which is stable to shipping at extreme temperatures and which has an extended product stability. The hematology control product is used to monitor automatic hematology instrument performance and to aid the customer in the repair of the unit on site with minimal service representative intervention.

SUMMARY OF THE INVENTION

The present invention relates to a hematology control product for automated hematology instruments comprising an aqueous solution of at least one blood cell analog, an absorbance agent in an amount sufficient to simulate a predetermined hemoglobin concentration, and a stabilizing agent in an amount sufficient to stabilize the size of the blood cell analog when said control product is subjected to temperature ranging from −15° C. to 45° C.

In addition, the present invention relates to a method of using a control product on an automated blood analyzer comprising steps of a) diluting and mixing an aliquot of a control product with a blood diluent; b) aspirating an aliquot of the diluted control product from step a) and further diluting and mixing with a blood diluent; c) analyzing the diluted control product from step a) by impedance method to simulate a white blood cell count; d) analyzing the further diluted control product from step b) by impedance method to simulate a red blood cell and platelet counts.

As will be better appreciated from the following Detailed Description of Preferred Embodiments, the invention is particularly advantageous compared to the prior art in that it provides a temperature stable hematology control product suitable for automated hematology instruments. The invention will be better understood from the following description of preferred embodiments.

DETAILED DESCRIPTION OF PREFERRED EMBODIMENTS

In the present invention, a stable hematology control product for automated hematology instruments is provided.

The control product comprises an aqueous solution of at least one blood cell analog, an absorbance agent in an amount sufficient to simulate a predetermined hemoglobin concentration at a predetermined wavelength, and a stabilizing agent in an amount sufficient to stabilize the size of the blood cell analog when said control product is subjected to temperature ranging from −15° C. to 45° C. The hematology control product is used to monitor hematology instrument performance and to aid in the repair of the instrument on site with minimal service representative intervention. Moreover, the control product finds particular applicability in support of hematology instruments in the developing markets where temperature control or refrigeration is not readily available.

The control product finds wide utility because it is stable under stressful shipping conditions at temperature ranging from −15° C. to 45° C. In addition, the control product has an extended product stability of greater than six months and preferably greater than one year without any necessary refrigeration. After initial opening of the control product vial, the control product is stable (open vial stability) for at least thirty days without any necessary refrigeration. For the purposes of this invention, a control product is defined as "stable" or having "stability" providing the control product contains a consistent size within 20%, preferably 10%, of the original size of the blood cell analogs and the absorbance agent functions to simulate a predetermined hemoglobin concentration at a predetermined wavelength for a time period after being exposed to a broad range of storage temperatures.

Figure 2:
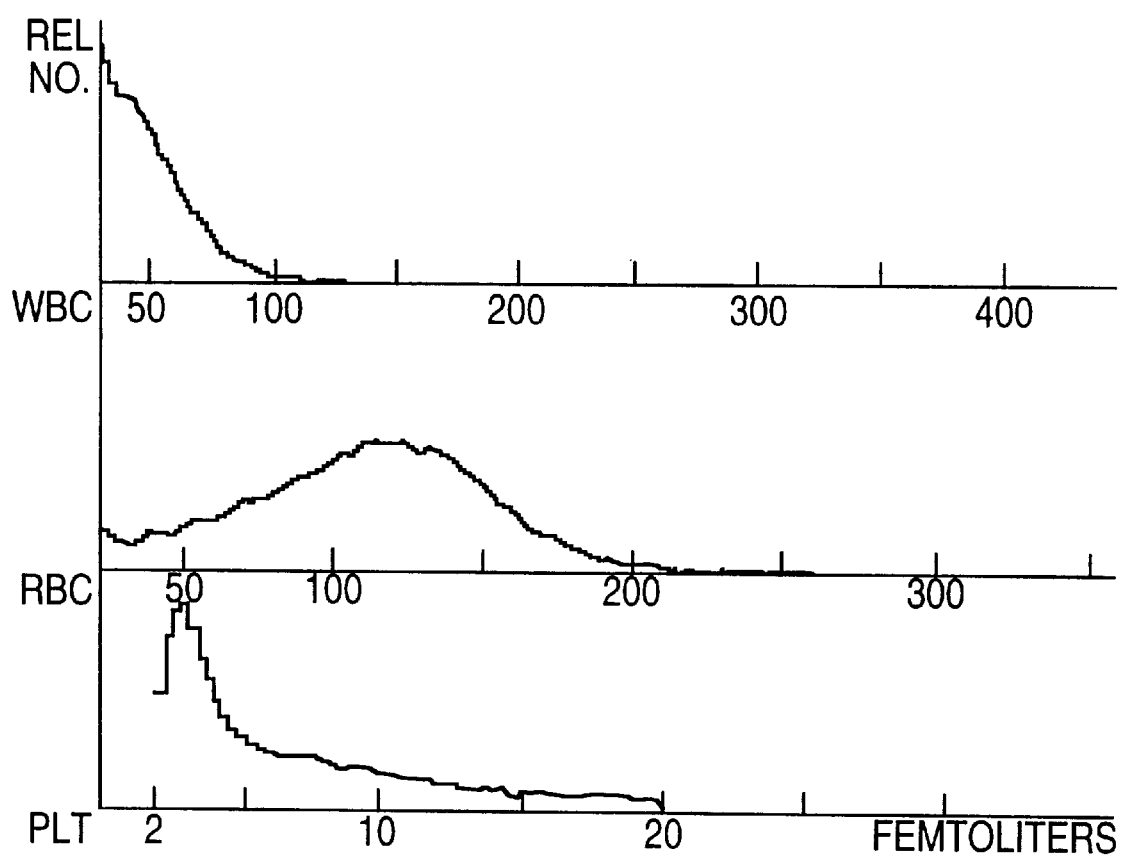
FIG. 2 illustrates a histogram of a commercial hematology control product containing three white blood cell analogs and stabilized red blood cells which has been subjected to a temperature of 45° C. for 3 days.
Figure 3:
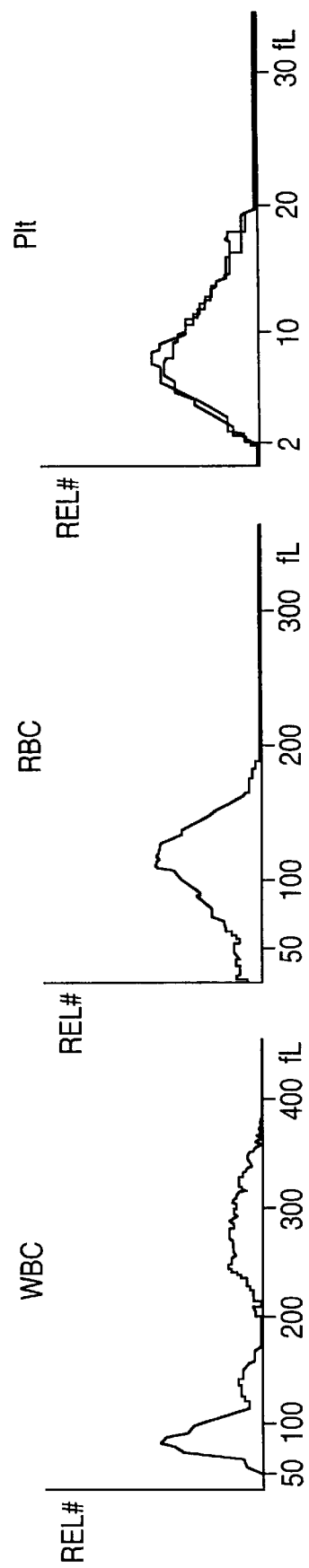
FIG. 3 illustrates a histogram of a commercial hematology control product containing three white blood cell analogs and stabilized red blood cells which has been frozen for 2 hours and thawed.

When a commercial hematology control product is subjected to temperature ranging −15° C. to 45° C., the control product is no longer useful for quality control measurements. As seen in FIG. 2, wherein the product is subjected to 45° C. for three days, the size of the white blood cell analogs, stabilized red blood cells and platelet analogs are distorted such that the control product is no longer useful for quality control measurements. As seen in FIG. 3, wherein the product is subjected to freezing for two hours and then thawing, the size distributions of the white blood cell analogs and stabilized red blood cells are shifted to the left and there is an indication of the presence of red blood cell ghosts from lysed red blood cells. Consequently, this control product is no longer useful for quality control measurements.

The blood cell analog can be made from a variety of raw materials, including human and non-human, red and white blood cells, and plastic particles prepared by methods known to those skilled in the art. The blood cell analog can range in size from about 35 to about 450 fL, and will have a size distribution of the blood cell analog consistent with human blood. Representative methods for preparing a blood cell analog are found in U.S. Pat. Nos. 4,704,364 and 5,389,664 to Carver et al.; 3,574,137 and 3,640,896 to Decasperis; 3,873,467 to Hunt; 5,262,327 and 5,207,208 to Ryan; 4,219,440 to Runck et al.; and 5,320,964 Young et al, which are hereby incorporated by reference. In a preferred embodiment, a blood cell analog is prepared from human red blood cells according to the procedure detailed in Example 1. This procedure is further detailed in U.S. Pat. Nos. 5,380,664. In a more preferred embodiment, three leukocyte blood cell analogs are prepared by the methods disclosed in U.S. Pat. No. 5,380,664.

The hematology control product contains an absorbance agent, such as a dye, in an amount sufficient to simulate a predetermined hemoglobin concentration at a predetermined wavelength. Most hemoglobin chromogens measured on automated hematology instrument absorb light at different wavelengths in the 500–650 nm range. The wavelength and concentration of the dye in the hematology control product will depend upon the type of hemoglobin chromogen and hemoglobin concentration being measured by the hematology instrument. By altering the concentrations of the dye in the hematology control product, the product can simulate blood sample having various levels of hemoglobin concentrations.

In basic automated hematology instruments which merely measure total hemoglobin, the selection of the dye will be within the absorbance wavelength of the instrument, typically from 450 to 675 nm, to provide quality assurance that the instrument is operational. Preferably the hematology control product contains a concentration of dye which enables a hemoglobin measurement of approximately 8 grams per 100 ml of blood.

It has been found that several dyes can be used for the present invention. Representative dyes include monoazo monochlorotriazinyl dyes, such as Cibacron Brilliant Red 3B-A, pyrimidinyl dyes, such as Procion Brilliant Red HE-7B; Poncau 3R Red Dye (CI 16155); and FD&C Red #40. As appreciated by those skilled in the art, the selection of an absorbance agent will include a consideration of it being compatible with other components in the hematology control product. In addition, it is preferred that the dye has a red color so that it visually simulates the color of fresh blood. More preferably the dye is Cibacron Brilliant Red 3B-A.

A stabilizing agent is added to provide blood cell analog stability through freezing and thawing conditions of temperatures ranging from −15° C. to 45° C. The stabilizing agent enables the hematology control product to be transported without need for a temperature controlled environment, such as refrigeration. Suitable stabilizing agents are salts, polyols, and dimethyl sulfoxide. The preferred stabilizing agent is selected from glycerol, ethylene glycol and propylene glycol and mixtures thereof. The most preferred stabilizing agent is glycerol. When glycerol is used, it not only stabilizes the blood cell analog through freezing conditions, but also enhances the suspension characteristics of the blood cell analog in the aqueous solution of the control product.

In the preferred embodiment, the stabilizing agent is used at a concentration of about 5% to about 30%, preferably about 15% to about 25% (v/v). The addition of the stabilizing agent has been found to affect the osmolality of the aqueous solution. Moreover, it has been found that the osmolality of the solution affects the stability of the hematology control product. More specifically, the osmolality affects the temperature at which the hematology control product freezes. In the preferred embodiment, the osmolality of the hematology control product ranges from about 1,800 to about 2,800 mOsm, preferably from about 2,000 to about 2,600 mOsm.

In a first embodiment, it has been discovered that a single blood cell analog can function to provide a white blood cell count and a red blood cell count. More specifically, it has been found that by varying the dilution of the hematology control product enables the hematology control product to perform both red blood cell count and white blood cell count quality control functions. Example 4 provides an example and further explanation of using this embodiment.

In a second embodiment of the present invention, the hematology control product contains three different blood cell analogs which function as three different subpopulations of leukocyte analogs. Suitable leukocyte analogs can be prepared by methods known to those skilled in the art. However, in a preferred embodiment, the three leukocyte analogs are prepared by the method disclosed in U.S. Pat. Nos. 4,704,364 and 5,389,664 to Carver et al. Carver et al. teach a method to prepare blood cell analogs in the size range of 35 fL to 90 fL to represent lymphocyte blood cells, 90 fL to 160 fL to represent monocyte blood cells and 160 fL to 450 fL to represent granulocyte blood cells.

In a third embodiment of the present invention, the hematology control product further contains a platelet analog. The platelet analog can vary in size, but should not overlap the size of the blood cell analog. Typically, the platelet analog will range in size from 2 to 30 fL, preferably 8 to 15 fL. The size distribution of the platelet analog will be consistent with platelets contained in human blood.

The platelet analog can be made from a variety of raw materials, including human and non-human, red and white blood cells, and plastic particles. Preferably, the platelet analog is made from goat red blood cells. The goat cells are prepared using fixative solution, typically an organic aldehyde, including monoaldehydes such as formaldehyde, or dialdehydes such as glutaraldehyde. Glutaraldehyde is the preferred aldehyde, since It reacts more rapidly than formaldehyde.

Although most room temperature fixation with glutaraldehyde occurs within two hours, more time is required for the blood cells to be totally resistant to the usual red blood cell lytic agents employed in automated hematology instruments. The goat blood cells are treated with the fixative solution in order that the platelet analogs retain its size within 10% of the original size when used in the automated hematology instruments. In addition, the fixation also stabilizes the platelets when the platelet is subjected to temperature ranging from −15° C. to 45° C.

The length of time for fixation with glutaraldehyde will range between 2 and 72 hours, preferably between 3 to 30 hours depending upon temperature, concentration of glutaraldehyde and number of cells. Underfixation results in blood cells which are lyseable when subjected to the lytic reagents. More specifically, contrary to the prior art, such as U.S. Pat. No. 5,008,201, the platelet analog is not lyseable when used in the automated hematology instrument. In a preferred embodiment, the platelet analog is prepared by the method of Example 2.

When the preferred platelet analog is prepared, it has been found that a surfactant should be added to the hematology control product to prevent the platelet from aggregating or adhering to surfaces of the container or instrument. The surfactant should have a high hydrophile lipophile balance (HLB). The HLB typically has a value greater than 15 and more preferably greater than 17. Typically, the surfactant is in an amount effective to inhibit the platelet analogs from aggregating or adhering to surfaces of the container or instrument without adversely affecting the blood cell analog. As appreciated by those skilled in the art, the effective amount of surfactant can be empirically determined, but is typically less than 0.5% by weight of the control product. Suitable surfactants include non ionic surfactants including alkyl polyether alcohols. Suitable commercial examples of these surfactants include Diazopan® SS-837 by GAF Chemical Corp., Triton® X405 by Rohm and Hass, and Pluronic® F 68 by BASF Wyandotte Corp. and Tween® 20 by J. T. Baker. Preferably the surfactant is Tween® 20.

In addition, it is also desirable to include in the hematology control product a sufficient amount of a preservative to prevent the growth of bacteria or fungi in the aqueous solution or on the analog particles. More particularly, the preservative is preferably a fungicide and/or a bactericide which is compatible with the other components of the hematology control product. The preservatives are known to those skilled in the art.

Features and advantages of the present invention are more fully shown with respect to the following non-limiting examples.

EXAMPLE 1

Method of Making a Blood Cell Analog

The following is a specific example of preferred reagents and recommended specific procedural steps for treating human red blood cells to obtain a blood cell analog. It will be understood that the formulations and the procedures are only illustrative and that other ingredients, proportions and procedures can be employed, in accordance with the disclosures in this invention.

Fresh Blood Wash Solution And Washing And Resuspending Solution For Fixed Cells (WRS) (Phosphate Buffered Saline-Liter Formulation)

| | | |
|---|---|---|
| 1. | Sodium phosphate monobasic | 0.2 g |
| 2. | Sodium phosphate dibasic .7H$_2$O | 2.0 g |
| 3. | Sodium azide | 0.1 g |
| 4. | Sodium chloride | 9.4 g |
| 5. | q.s. to 1 liter with distilled water pH 7.3 to 7.5 osmolality 320 to 340 mOsm/kg. | |

Erythrocyte Diluting Solution

| | | |
|---|---|---|
| 1. | Sodium chloride | 6.96 g |
| 2. | Potassium chloride | 0.30 g |
| 3. | Sodium phosphate monobasic | 1.31 g |
| 4. | Sodium phosphate dibasic .7H$_2$O | 10.85 g |
| 5. | q.s. to 1 liter with distilled water pH 7.3 to 7.5 osmolality 320 to 340 mOsm/kg. | |

Procedure:

1. Select human red blood cells having a mean cell volume range of about 81 to 89 fL and red cell distribution width of less than 18 fL. Wash the packed human red blood cells with the Fresh Blood Wash Solution.

2. Dilute the washed packed cells with the Erythrocyte Diluting Solution to a count of 1×10$^6$/uL.

3. Prepare a glutaraldehyde fixative reagent having a glutaraldehyde concentration of about 1.0% to 10% by adding a commercial 25% glutaraldehyde product to the Erythrocyte Diluting Solution. The preferred concentration is 5%.

4. Add a measured amount of the fixative of step 3 to the washed red blood cell suspension to obtain a final glutaraldehyde concentration of 0.1% to 1.0%, and mix for about 20 minutes. Transfer to sealed containers which are rolled slowly for 12 to 72 hours.

5. Centrifuge the fixed cells at about 400 RCF for about 5 minutes. Remove the supernatant fluid, wash cells several times with the Fresh Blood Wash Solution (WRS), then resuspend in the Washing and Resuspending Solution (WRS).

6. Determine the mean cell volume to make certain that fixation is complete. Partial fixation will show a drop in volume after the addition of 10% LYSE S® II reagent in ISOTON® II diluent (Coulter Corporation, Miami, Fla.). A totally fixed red blood cell shows less than a 5 fL change in apparent volume.

7. For a stand alone lymphocyte control, resuspend the washed fixed cells in the resuspending solution and adjust the concentration to simulate that of human lymphocytes in normal human blood.

8. For multiple hematological controls, resuspend the washed fixed cells in the media for the multiple parameter hematology control, the cell count being appropriate to measure lymphocytes.

9. The fixed cells can be stored for a time period of at least six months.

In accordance with the above example, but using formaldehyde in place of glutaraldehyde, the final concentration of formaldehyde is 2.5% to 10%. The time required for fixation with formaldehyde is longer than with glutaraldehyde.

EXAMPLE 2

Method of Making a Platelet Analog

1. Obtain fresh goat whole blood with an MCV of 12 to 16 fL.

2. Wash the red blood cell with suitable washing solution to remove unwanted cellular components, such as white blood cells, platelets, plasma, and plasma proteins.

3. Washed goat red blood cells are added to a glutaraldehyde fixative solution whereby the final glutaraldehyde concentration is 1% based upon a goat red blood cell count of approximately 1,000,000 cells per microliter.

4. The fixation occurs for 16 to 32 hours at ambient temperature.

5. Fixed cells are washed to remove residual glutaraldehyde.

6. The resultant fixed cells are suspended in a antimicrobial media at a known cell count.

Example 3

Control Product Assembly

A hematology control product is formulated as follows:

A sufficient number of blood cell analogs prepared by Example 1 to achieve an approximate concentration of 6000 to 60,000 particles per microliter; a sufficient number of platelet analogs to achieve an approximate concentration of 1000 to 3000 particles per microliter; a aqueous solution of dye at a concentration 0.75 to 1.5 grams per liter to simulate a 6 to 12 grams per liter hemoglobin measurement; 15% to 25% Glycerol (v/v) of the suspending media; and 0.001% to 1.0% (v/v) Tween® 20 are added together to form a hematology control product.

In a more preferred formulation approximately 36,000 blood cell analogs, prepared by Example 1; approximately 2000 platelet analogs prepared by Example 3 and an aqueous solution of Cibacron Brilliant Red at an approximate concentration of 1 gram per liter to simulate an 8 grams per liter hemoglobin concentration; 17% Glycerol (v/v) of the suspending media; and 0.5% (vv) Tween® 20 are added together to form a hematology control product.

EXAMPLE 4

Method of Using Blood Cell Analog to Simulate Red and White Blood Cells

Figure 1:
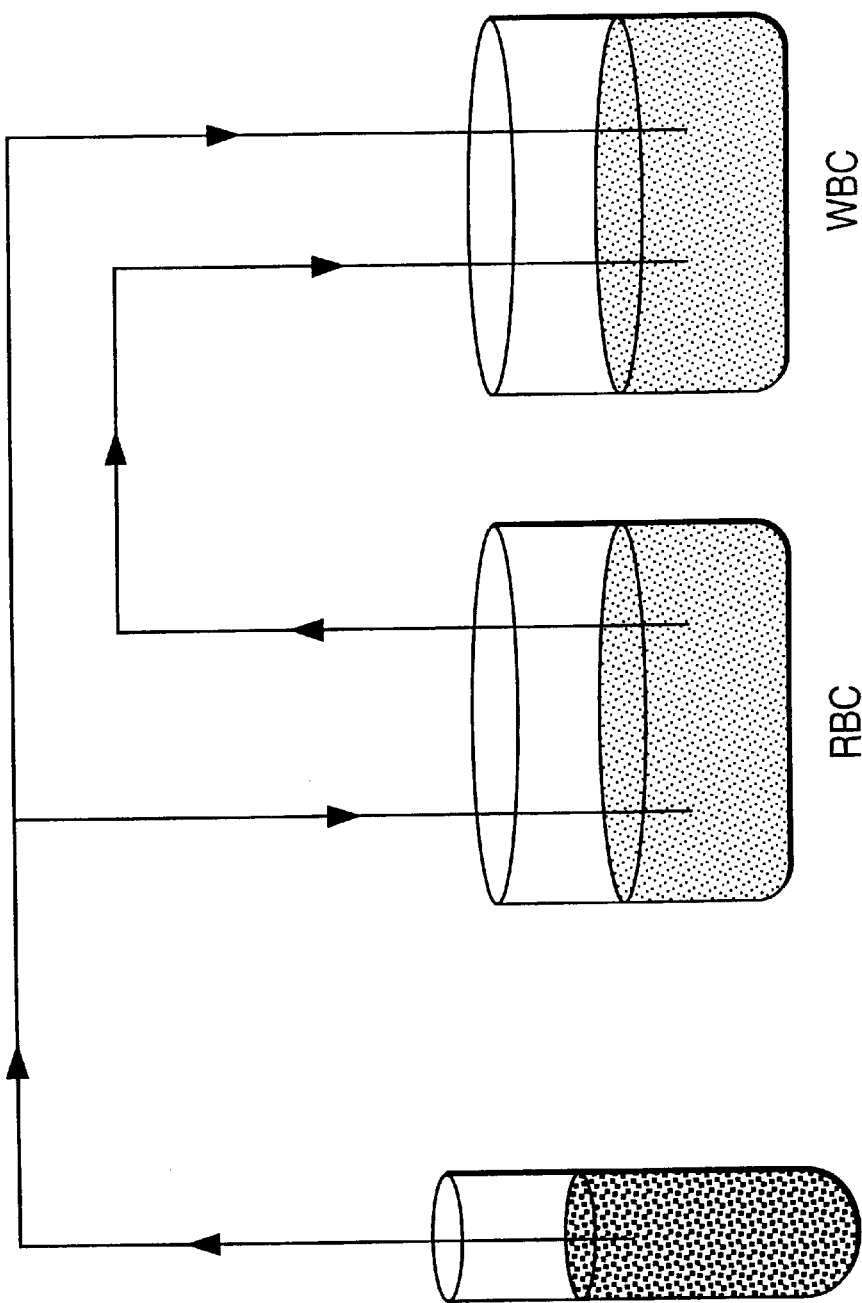
FIG. 1 illustrates a fluid distribution system for an embodiment of the ematology control product.

When the control product is used in the following manner, quality control of the automated hematology instrument reagent pumps and cell detectors can be obtained using only a single blood cell analog. In this Example, the blood cell analog contained in the hematology control product prepared according to the preferred formulation of Example 3 functions to provide a white blood cell (WBC) count and red blood cell (RBC) count by controlling the concentration of the number of blood cell analogs contained in WBC and RBC sample receiving vessels. Referring now to FIG. 1, the following steps are performed.

1. 40 microliters ($\mu$L) of a hematology control product is aspirated from a sample tube into a WBC sample receiving vessel containing 2.54 milliliters (mL) of a suitable blood diluent, such as ISOTON® III.

2. 0.42 milliliters (mL) of a lytic reagent is added to the WBC sample receiving vessel and a hemoglobin measurement is made.

3. The WBC sample receiving vessel is flushed to remove residuals of the hematology control product.

4. 45 $\mu$L of the hematology control product is aspirated from a sample tube into a RBC sample receiving vessel, containing 2.484 milliliters (mL) of a suitable blood diluent, such as ISOTON® III.

5. The mixture in the RBC sample receiving vessel is mixed to insure a homogeneous suspension of blood cell analogs.

6. 200 $\mu$L of the suspension in the rbc sample cup is removed and delivered to the WBC sample receiving vessel which contains 2.54 milliliters (mL) of a suitable blood diluent, such as ISOTON® III.

7. The WBC sample receiving vessel is mixed to insure a homogenous suspension of blood cell analogs.

8. A white blood cell count is made from the contents contained in the WBC sample receiving vessel and a red blood cell count and related red blood cell parameters are made from the contents contained in the RBC sample receiving vessel. When the hematology control product contains platelet analogs, a platelet count is made from the contents contained in the RBC sample receiving vessel.

In the preceding example, if the automatic hematology instrument was properly functioning, the instrument would measure a WBC count of approximately 10,000, a RBC count of approximately 4,000,000; a hemoglobin concentration of approximately 8 g/100 ml; and optionally, a platelet count of approximately 250,000.

While certain representative embodiments and details have been shown for the purpose of illustrating the invention, various changes and modifications can be made therein without departing from the scope of the invention as defined in the appended claims.

What is claimed is:

1. A hematology control product for automated hematology instruments comprising an aqueous solution of:
   a) at least one blood cell analog;
   b) an absorbance agent in an amount sufficient to simulate a predetermined hemoglobin concentration measurement at a predetermined wavelength; and
   c) a stabilizing agent in an amount sufficient to stabilize the size of the at least one blood cell analog when said control product is subjected to temperatures ranging from −15° C. to 45° C.

2. The hematology control product of claim 1, wherein the absorbance agent comprises a red dye in an amount sufficient to simulate a predetermined hemoglobin concentration at a predetermined wavelength of 500 to 550 nm.

3. The hematology control product of claim 1, which further comprises a platelet analog which does not lyse when analyzed in an automated hematology instrument.

4. The hematology control product of claim 3, wherein said stabilizing agent is glycerol.

5. The hematology control product of claim 1, wherein said control product comprises blood cell analogs of three different subpopulations of leukocytes.

6. The hematology control product of claim 1, wherein said at least one blood cell analog functions to provide a white blood cell (WBC) count and a red blood cell (RBC) count.

7. The hematology control product of claim 1, wherein said product has an osmolality from about 1,800 mOsm to about 2,800 mOsm.

8. A method of using a control product on an automated blood analyzer comprising the steps of:

a) diluting and mixing an aliquot of a hematology control product with a blood diluent;

b) aspirating an aliquot of the diluted control product from step a) and further diluting and mixing said aliquot with a blood diluent;

c) analyzing the diluted control product from step a) by an impedance method to simulate a white blood cell count; and d) analyzing the diluted aliquot from step b) by an impedance method to simulate a red blood cell count.

9. The method of claim 8 further comprising analyzing the diluted aliquot from step b) by an impedance method to simulate a platelet count.

10. The method of claim 8 which further comprises the steps of:

e) adding an amount of lysing reagent to the diluted control product from step a); and f) measuring absorbance of the diluted control product from step e) at a predetermined wavelength to simulate a hemoglobin concentration.

11. The method of claim 8, wherein the control product comprises:

a) at least one blood cell analog;

b) an absorbance agent in an amount sufficient to simulate a predetermined hemoglobin concentration measurement at a predetermined wavelength; and c) a stabilizing agent in an amount sufficient to stabilize the size of the at least one blood cell analog when said control product is subjected to temperature ranging from −15° C. to 45° C.

12. The method of claim 11, wherein the control product further comprises a platelet analog.

13. The method of claim 8, wherein the hematology control product contains a single blood cell analog which is used to simulate both red blood cells and white blood cells on an automated hematology instrument.

14. The method of claim 8, wherein said hematology control product comprises blood cell analogs of three different subpopulations of leukocytes.

* * * * *